(12) United States Patent
Oesterreich et al.

(10) Patent No.: US 9,022,981 B2
(45) Date of Patent: May 5, 2015

(54) CLAMP MOUNTING FOR A SYRINGE OF A DOSING APPARATUS, DOSING APPARATUS AND BLOOD TREATMENT APPARATUS

(75) Inventors: Stefan Oesterreich, Neu-Anspach (DE); Martin Stejskal, Bad Soden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/360,969

(22) Filed: Jan. 30, 2012

(65) Prior Publication Data
US 2012/0195793 A1  Aug. 2, 2012

Related U.S. Application Data

(60) Provisional application No. 61/437,690, filed on Jan. 31, 2011.

(30) Foreign Application Priority Data

Jan. 31, 2011 (DE) .......................... 10 2011 009 905

(51) Int. Cl.
| | |
|---|---|
| *A61M 5/00* | (2006.01) |
| *A61M 5/14* | (2006.01) |
| *A61M 1/00* | (2006.01) |
| *A61M 1/16* | (2006.01) |

(Continued)

(52) U.S. Cl.
CPC ............... *A61M 1/16* (2013.01); *A61M 1/3672* (2013.01); *A61M 2209/082* (2013.01); *A61M 5/1415* (2013.01); *A61M 5/1417* (2013.01); *A61M 5/1452* (2013.01); *A61M 5/1458* (2013.01)

(58) Field of Classification Search
CPC .......................................... A61M 5/142–5/155

USPC ........ 604/4.01, 5.01, 6.01, 67, 131, 152, 154; 422/44

See application file for complete search history.

(56) References Cited

U.S. PATENT DOCUMENTS

| | | | | | |
|---|---|---|---|---|---|
| D327,123 | S | * | 6/1992 | Stracener et al. | ............. D24/111 |
| 5,254,096 | A | * | 10/1993 | Rondelet et al. | ............... 604/152 |

(Continued)

FOREIGN PATENT DOCUMENTS

| | | |
|---|---|---|
| WO | 97/02056 A1 | 1/1997 |
| WO | 2007/012915 A1 | 2/2007 |

OTHER PUBLICATIONS

PCT International Search Report for PCT/EP2012/000367, mailed on May 21, 2012.

*Primary Examiner* — Philip R. Wiest
*Assistant Examiner* — Benjamin Klein
(74) *Attorney, Agent, or Firm* — Kenyon & Kenyon LLP

(57) ABSTRACT

The present invention relates to a clamp mounting for accommodating at least one section of a drug delivery device or for restricting it in at least one direction of motion. The drug delivery device features an accommodation chamber for the drug solution or substance to be delivered. The clamp mounting features at least one clamping device. The clamping device features at least one recess which is provided for accommodating or restricting at least one part of the section of the drug delivery device. The recess or at least a section hereof has an arched or curved demarcation between itself and sections of the clamping device that are not recessed. Alternatively or additionally, the recess or at least a section hereof is arched or curved in at least one section hereof. The present invention further relates to a dosing apparatus and a blood treatment apparatus.

11 Claims, 6 Drawing Sheets

(51) Int. Cl.
*A61M 1/36* (2006.01)
*A61M 5/145* (2006.01)

(56) References Cited

U.S. PATENT DOCUMENTS 5,295,966 A * 3/1994 Stern et al. .................... 604/154
5,295,967 A * 3/1994 Rondelet et al. .............. 604/154
5,545,140 A * 8/1996 Conero et al. ................. 604/154
5,948,251 A * 9/1999 Brugger ........................ 210/252
6,808,149 B1 10/2004 Sendowski et al.
2007/0191787 A1* 8/2007 Lim et al. ...................... 604/246

* cited by examiner

CLAMP MOUNTING FOR A SYRINGE OF A DOSING APPARATUS, DOSING APPARATUS AND BLOOD TREATMENT APPARATUS

CROSS-REFERENCE TO RELATED APPLICATIONS

The present application claims priority to U.S. Provisional Application Ser. No. 61/437,690, filed on Jan. 31, 2011, and claims priority to Application No. DE 10 2011 009 908.5, filed in the Federal Republic of Germany on Jan. 31, 2011, each of which is expressly incorporated herein in its entirety by reference thereto.

FIELD OF INVENTION

The present invention relates to a clamp mounting. It further relates to a dosing apparatus and a blood treatment apparatus.

BACKGROUND INFORMATION

Dosing apparatuses are known from medical practice. In dosing apparatuses of this kind, a syringe or a different drug delivery device is inserted which contains a medical liquid fluid—e.g., heparin that was extracorporeally added during a blood treatment such as a hemodialysis. The fluid is delivered as needed or according to a setting by means of the dosing apparatuses.

SUMMARY

One object of the present invention is to propose a further clamp mounting of the above kind.

The clamp mounting according to the present invention is provided for accommodating at least one section of a drug delivery device within a medical dosing apparatus (hereafter also shortly referred to as: dosing apparatus) or for restricting the section in at least one direction of motion. The drug delivery device features an accommodation chamber for the drug solution or substance to be delivered. The clamp mounting features at least one clamping device which is provided for supporting, restricting, accommodating the section, for limiting mobility of the section—or a part hereof—of the drug delivery device and/or for moving the section. The clamping device features at least one recess which is provided for accommodating the section—or a part hereof—of the drug delivery device or for restricting it.

The recess features a demarcation between itself and other sections of the clamping device or sections of the clamping device that are adjacent to the section or it features an edge or represents such. The recess, the demarcation and/or the edge or a part hereof, respectively, is or are arched, curved, bent or the like.

The object according to the present invention is also accomplished by means of a dosing apparatus, which features at least one clamp mounting according to the present invention.

The object according to the present invention is also accomplished by means of a blood treatment apparatus, which features at least one clamp mounting according to the present invention or at least one dosing apparatus according to the present invention.

Advantageous developments and particular designs of the present invention are described in the exemplary, non-limiting embodiments.

Embodiments according to the present invention may have one or more of the features described hereafter.

In all of the following embodiments, the use of the expression "may be" or "may have," and so on, is to be understood synonymously with "preferably is" or "preferably has," respectively, and so on, and is intended to explain certain embodiments according to the present invention.

The arc or curve of the recess, the demarcation, the edge or the part is in certain embodiments every course which as a whole or over at least an area hereof is other than straight, i.e., is not straight.

The recess in the clamping device of the clamp mounting according to the present invention serves for limiting the mobility of a section of the drug delivery device. For example, an axial movability of the section may be limited by means of the recess. For example, the clamping device may inhibit an undesirable axial movability of the syringe piston. For this purpose, the aforementioned section is introduced into the recess and/or restricted by the recess during clamping of the drug delivery device in or with the clamping device and, after having been introduced or pushed underneath, can only be shifted or moved in its axial direction together with the clamping device.

The recess may be, e.g., a groove. This particular embodiment of the recess has the advantage that an undesired moving of the aforementioned section may be restricted in both axial directions (e.g., both backwards and forwards). Additionally, guiding or actively moving the section in both axial directions may be possible by means of a groove. A groove may easily ensure a play-free limitation or restriction.

However, the recess does not have to be a groove in order to serve its purpose. Rather, an effect of the groove in at least one axial direction—to stick with the example of the piston of a syringe—may also be achieved by providing a step or a ledge. Therefore, one of ordinary skill in the art would understand that the term "recess," as used herein, at the same time includes the possibility to design the recess as a step, groove, edge, ledge or the like. In certain embodiments according to the present invention, the recess is designed as a groove, in others as a ledge, and in again other embodiments as an edge or a ledge or the like.

In some embodiments according to the present invention, the recess is provided within or on the clamping device such that a first cross-section through the clamping device above the recess has the same shape as a second cross-section through the clamping device below the recess. In these embodiments, the recess may therefore represent a disruption, but not a border of the clamping device (e.g., towards its front end).

In some embodiments according to the present invention, the clamping device is embodied as a clamp jaw.

In some embodiments according to the present invention, the clamping device features at least one spring or is connected to such which causes or contributes to the clamping effect.

In certain embodiments according to the present invention, the clamping device features, consists of or is connected to elastic material, in order to cause or contribute to the clamping effect by means of the elasticity of the material.

The recess is, in some embodiments according to the present invention, designed to extend over a whole depth of the clamping device. In other embodiments according to the present invention, the recess is designed to extend only over a part of the depth of the clamping device.

In some embodiments according to the present invention, the recess or the demarcation is completely, or in at least an area hereof, curved or arched or bent or deviates from a straight course or line in another way. The deviation from the straight line in some embodiments according to the present invention relates—exclusively or additionally—to a plane parallel to a moving direction of the section which is limited in its mobility by means of the clamping device. The deviation from the straight line may be such that the course of the demarcation in a plane parallel to the moving direction of the section which is limited in its mobility by means of the clamping device is concave towards the section (which may be designed to be, e.g., syringe piston) and convex in a direction from a delivery opening for the drug.

The section of the drug delivery device may be a section which is arranged to be movable relative to the rest of the drug delivery device or other sections hereof. It may be provided, e.g., for being movable for the purpose of dosing.

In certain embodiments according to the present invention, the drug delivery device is a syringe, and the section of the drug delivery device is a piston which is shiftable or movable within the syringe with the purpose of delivering the drug.

In some embodiments according to the present invention, the clamp mounting features a support on which the drug delivery device rests in state of use and/or during drug delivery. In particular, it may rest there with its section which is limited in its mobility by means of the clamping device. The support features a rolling radius by or under which the support is rounded off at at least one transition of a supporting surface to a front surface or lateral surface.

In certain embodiments according to the present invention, the clamping device features at least one front area or front surface which features a curve or arc or an area that is delimited in curve- or arch-shape.

In certain embodiments according to the present invention, the clamp mounting features at least or exactly two clamping devices for accommodating the section. The clamping devices may in particular be designed to be equal or identical; however, they may also be designed to be different (e.g., as left or right clamping device or otherwise different).

In some embodiments according to the present invention, a nozzle or opening of the drug delivery device for delivering the contents hereof is designed having a screw thread. The screw thread may be provided for being connected to a tube (e.g., infusion tube), a hollow needle (cannula), a catheter, three-way cocks or the like. The screw thread may be designed to be a standardized connecting system (in particular a Luer-Lock).

In some embodiments according to the present invention, the dosing apparatus or drug delivery device is provided for conveying anticoagulation solutions, in particular for conveying citrate solutions or calcium solutions, further heparin solutions.

In certain embodiments according to the present invention, the blood treatment apparatus is a dialysis apparatus, in particular a hemodialysis apparatus, a hemofiltration apparatus, a hemodiafiltration apparatus or the like, in particular for an acute dialysis.

Certain embodiments according to the present invention feature one or more of the following advantages.

In certain embodiments according to the present invention, "robust removal" of, e.g., the syringe out of the dosing apparatus or from the treatment apparatus is possible without reason to fear damage hereby. The term "robust removal" in this context is understood as being a removal without applying the intrinsically expected caution or diligence. The latter may especially be observed during removal which is done under time pressure. A jamming or wedging of, e.g., the syringe piston, due to which it gets stuck in the support of the handle of the dosing apparatus, is advantageously prevented according to the present invention. At least, the probability of jamming or wedging may be reduced. This advantage is supported in that the section may advantageously be tilted due to the particular geometry of the recess.

According to the present invention, the user does not, for instance, have to release or open the one or more clamping devices separately. Rather, the particular geometry of the clamping device with its arched recess allows an automatic and smooth release of the clamping device from the section of the drug delivery device when the section is withdrawn from the dosing apparatus.

This advantageous effect may be enhanced by the arc of the front surface of the clamping device.

Advantageously, the clamping device according to the present invention is suited for accommodating different sizes and types of drug delivery devices. Thus, e.g., syringes with 30 ml volume and syringes with 50 ml volume may be used. They all may be removed from or taken off the dosing apparatus equally problem-free in the robust way described above. This is not limited to syringes of only one producer. In fact, products of different producers may be used.

The present invention on the one hand allows easy release of, e.g., a syringe from the dosing apparatus. On the other hand, the clamp mounting according to the present invention is able to safely hold, e.g., the piston of a syringe and to prevent it from, e.g., undesirably resolving from the handle of the dosing apparatus.

Hereafter, the present invention is exemplarily explained by means of the figures of the appended drawings in which identical reference numerals refer to same or identical components.

DETAILED DESCRIPTION

Figure 1:
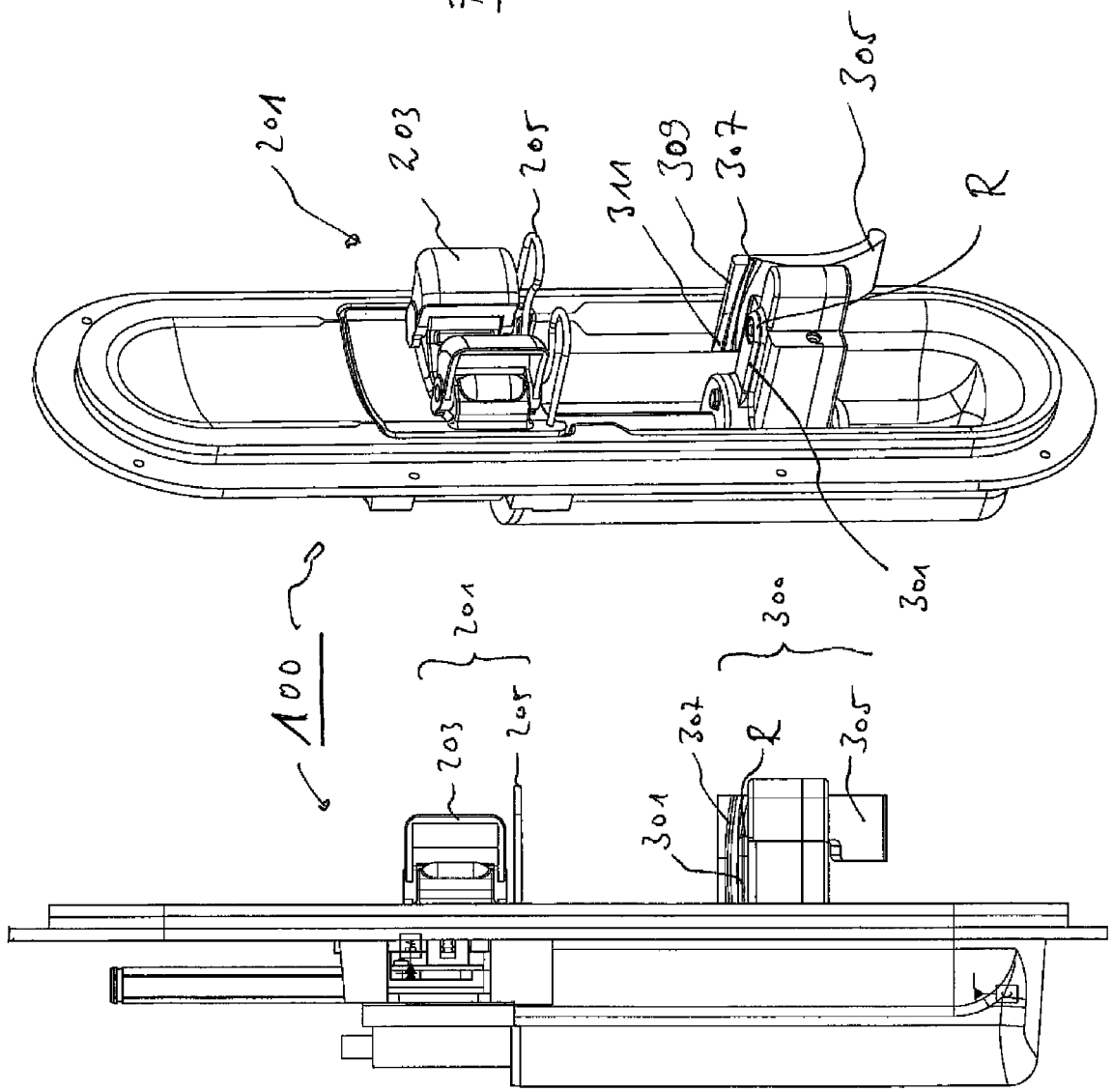
FIG. 1a shows a dosing apparatus according to the present invention in a lateral view.
FIG. 1b shows the dosing apparatus of FIG. 1a in perspective view.

FIG. 1a shows a dosing apparatus 100 according to the present invention (or at least the most relevant components hereof) in a lateral view. FIG. 1b shows the dosing apparatus of FIG. 1a in perspective view. Minor deviations in scale between the figures each from the side on the one hand and in perspective on the other hand are possible.

The dosing apparatus 100 features an (in relation to the illustration of the figure) upper mounting 201 for a syringe not shown in FIG. 1a and 1b as an example for a drug delivery device. The upper mounting 201 comprises a support or intake 203 and a bracket 205.

The dosing apparatus 100 further features a handle as a lower mounting, designed as clamp mounting 300 according to the present invention. The clamp mounting 300 features a support 301 on which the syringe not shown here may mount during its state of use. The support 301 has a rolling radius R under which it slopes in a curved manner at its narrow sides or sections hereof. The curve in which it slopes naturally does not necessarily have to be described with the indication of one single radius—even though it is denoted here. The mathematical formulation of the geometrical arc or curve may be more elaborate.

A piston or syringe piston of a syringe mounting on the support 301 and not shown here is—as can be recognized in the figures hereafter—as an example for the section of the drug delivery device supported by means of at least one clamping device 305 or restricted in at least one degree of freedom.

Indeed there is shown only one clamping device 305 each in FIGS. 1a and 1b. On the one hand, this serves for better illustration especially of a recess 307. The clamp mounting 300 may feature more than only one clamping device 305. For instance, a second clamping device facing the clamping device 305 shown may be provided. Additionally, in certain embodiments according to the present invention, a third one (as well as again further clamping devices) may be provided. On the other hand, the illustration of only one clamping device 305, as in FIG. 1a or 1b, serves for the person skilled in the art to recognize that the clamp mounting 300 according to the present invention in some embodiments may be used with only one clamping device 305. In such embodiments, a limiting stop, a step, a counter bearing or the like may be provided, together with which the clamping effect of the one clamping device 305 present on, e.g., the piston of a syringe may be generated.

Further, the recess 307 embodied as a groove is easily recognizable. The recess 307 is provided within the material respectively the width of the clamping device 305. If more than only one clamping device 305 is provided, such recess may only be embodied in one, each or some of the clamping devices.

The recess 307 extends in a horizontal direction of the dosing apparatus 100 of FIG. 1a and 1b (i.e., in a direction from right to left in these two figures) in a curve, however, not straight. In relation to FIGS. 1a and 1b, the curve is upwards convex and downwards concave. It is shown in FIG. 1a that the recess 307 extends over the whole depth of the clamping device 305 (i.e., in relation to the illustration of FIG. 1a, from left to right). In other embodiments, the recess 307 may, however, also extend over only a part of the depth of the clamping device 305.

A curve or arc 311 of a front surface 309 of the clamping device 305 can only hardly be recognized—and in principle only in FIG. 1b, however, not so much in FIG. 1a. The curve of the front surface 309—also—effects an arc of a section of the clamping device 305 in a top view of the front surface 309. The recognizable curve makes the front surface 309 narrower in a direction into the dosing apparatus 100; in sections which do not have an arc, the front surface 309 is broader. The arc 311 described here is independent of the arc of the recess 307.

Figure 2:
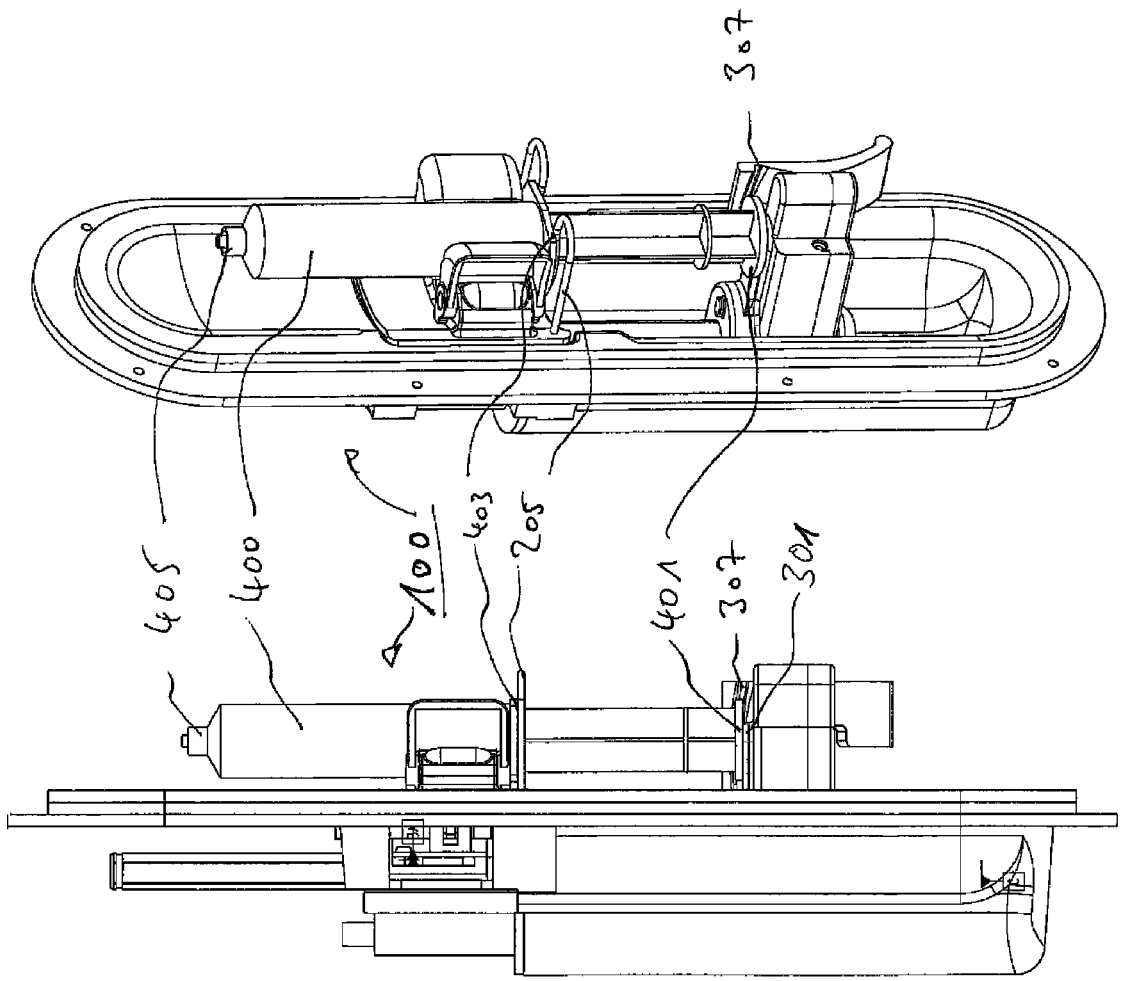
FIG. 2a shows the dosing apparatus of FIG. 1a, equipped with a syringe in its in-use disposition, in a lateral view.
FIG. 2b shows the dosing apparatus of FIG. 1b, equipped with a syringe in its in-use disposition, in perspective view.

FIGS. 2a and 2b show the dosing apparatus 100 of FIGS. 1a and 1b. FIGS. 2a and 2b differ from the illustrations of FIGS. 1a and 1b only in that additionally a syringe 400 is shown as an example of a drug delivery device. The syringe 400 features a syringe piston 401 (also shortly referred to as: piston 401) which in the in-use disposition of the syringe 400 or the dosing apparatus 100 shown in FIGS. 2a and 2b rests or mounts on the support 301. With another section 403 of the syringe 400, it further mounts on the bracket 205. The syringe 400 comprises a nozzle or an opening 405.

The recess 307 recognizably allows a tilting or twisting of the syringe 400 when it is being inserted in or taken out of the dosing apparatus 100.

With the beginning twisting motion of the syringe 400, the piston 401 is pushed against the support 301 under the rolling radius R. If the piston 401 or the syringe 400 continues tilting around its axis, the outer edge or the circumference of the piston 401 pushes the clamping device 305 against the spring effect over the arc of the front surface 309 into an opening position.

Figure 3:
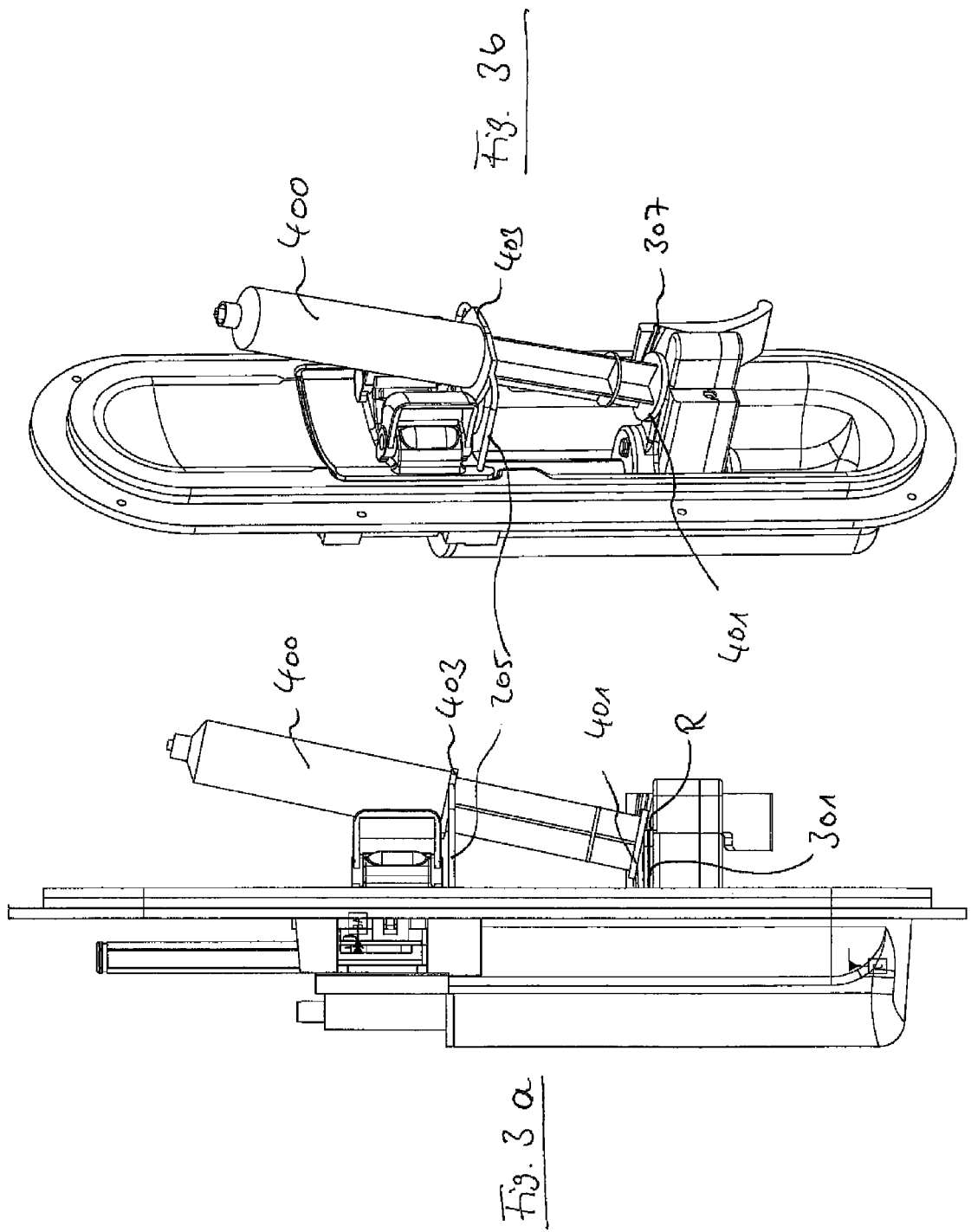
FIG. 3a shows the dosing apparatus of FIG. 2a during removal of the syringe from the dosing apparatus, in lateral view.
FIG. 3b shows the dosing apparatus of FIG. 2b during removal of the syringe from the dosing apparatus, in perspective view.

FIGS. 3a and 3b show the dosing apparatus 100 of FIGS. 2a and 2b, each during removal of the syringe 400 from the dosing apparatus 100.

The piston 401 of the syringe 400 may be rolled or gently tilted over the rolling radius R of the support 301.

The circumference of the piston 401 may retract into the arched recess of the front surface 309 during tilting of the piston 401. The arc of the recess matches the piston which during tilting with different diameters makes its way into the height of the recess and may provide for a smooth rise with which the clamping device 305 is pushed outwards against a spring effect.

Figure 4:
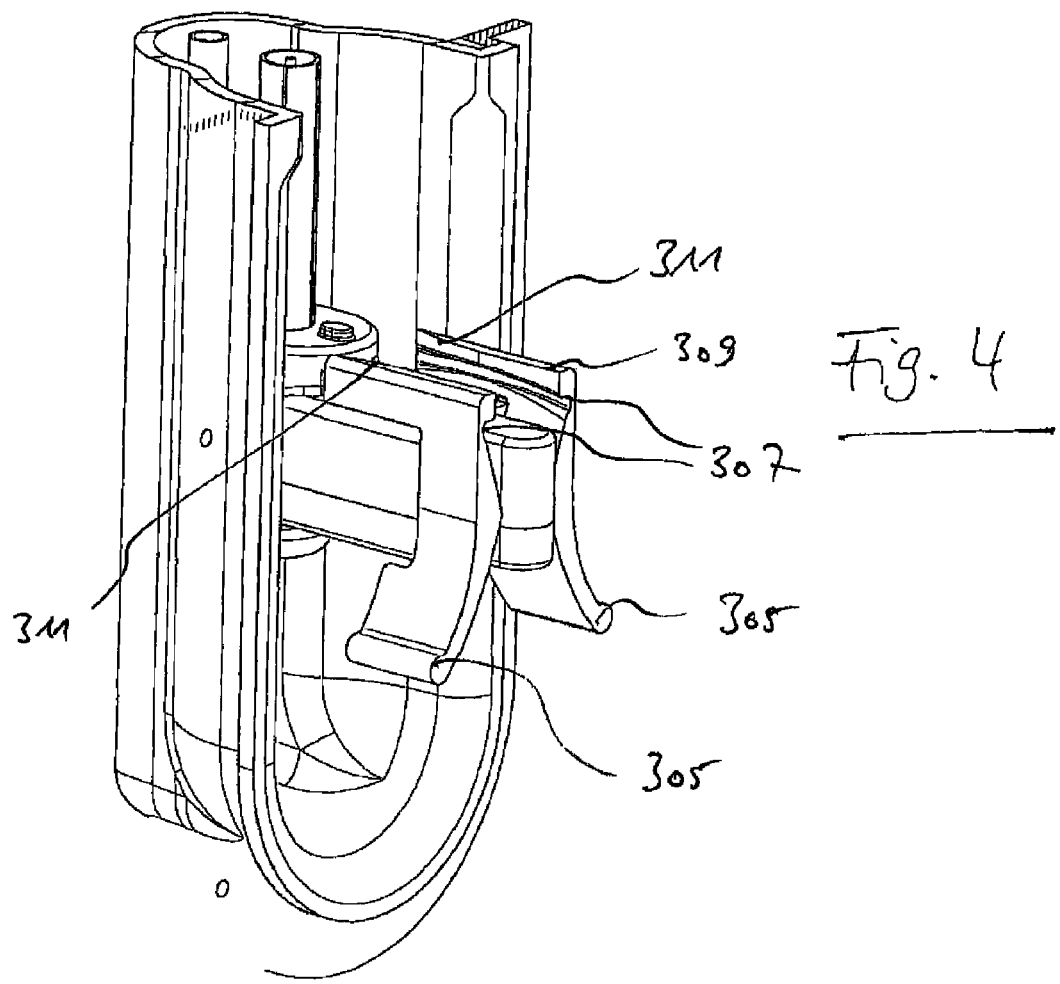
FIG. 4 shows a part of the clamp mounting according to the present invention in a sectional view.

FIG. 4 shows a part of the clamp mounting 300 according to the present invention in a sectional view. FIG. 4 shows two opposing clamping devices 305 each having one arched recess 307. The recesses 307 each extend below each of the front surfaces 309. The arc 311 of the front surface 309 can be seen on both clamping devices 305.

Figure 5:
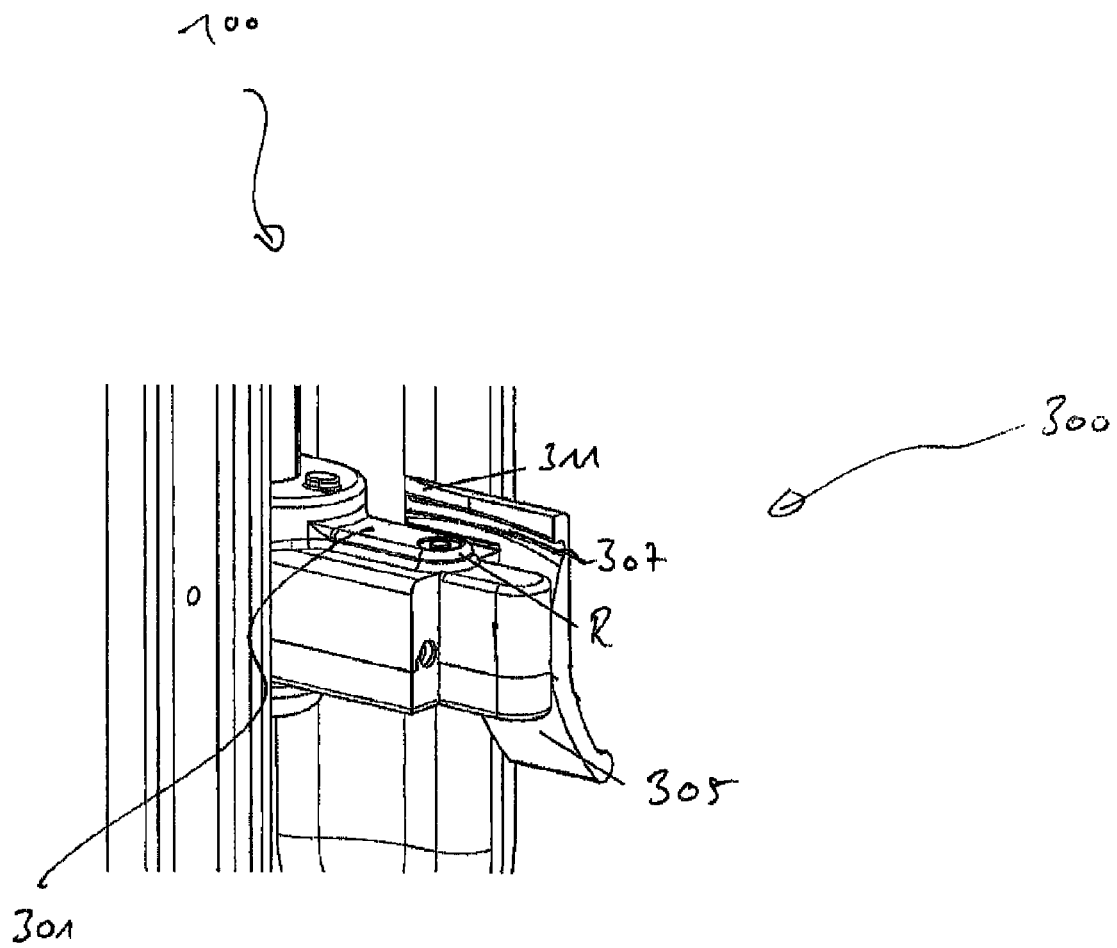
FIG. 5 shows an enlarged detail of the illustration of FIG. 1b.

FIG. 5 shows an enlarged detail of the illustration of FIG. 1b.

Figure 6:
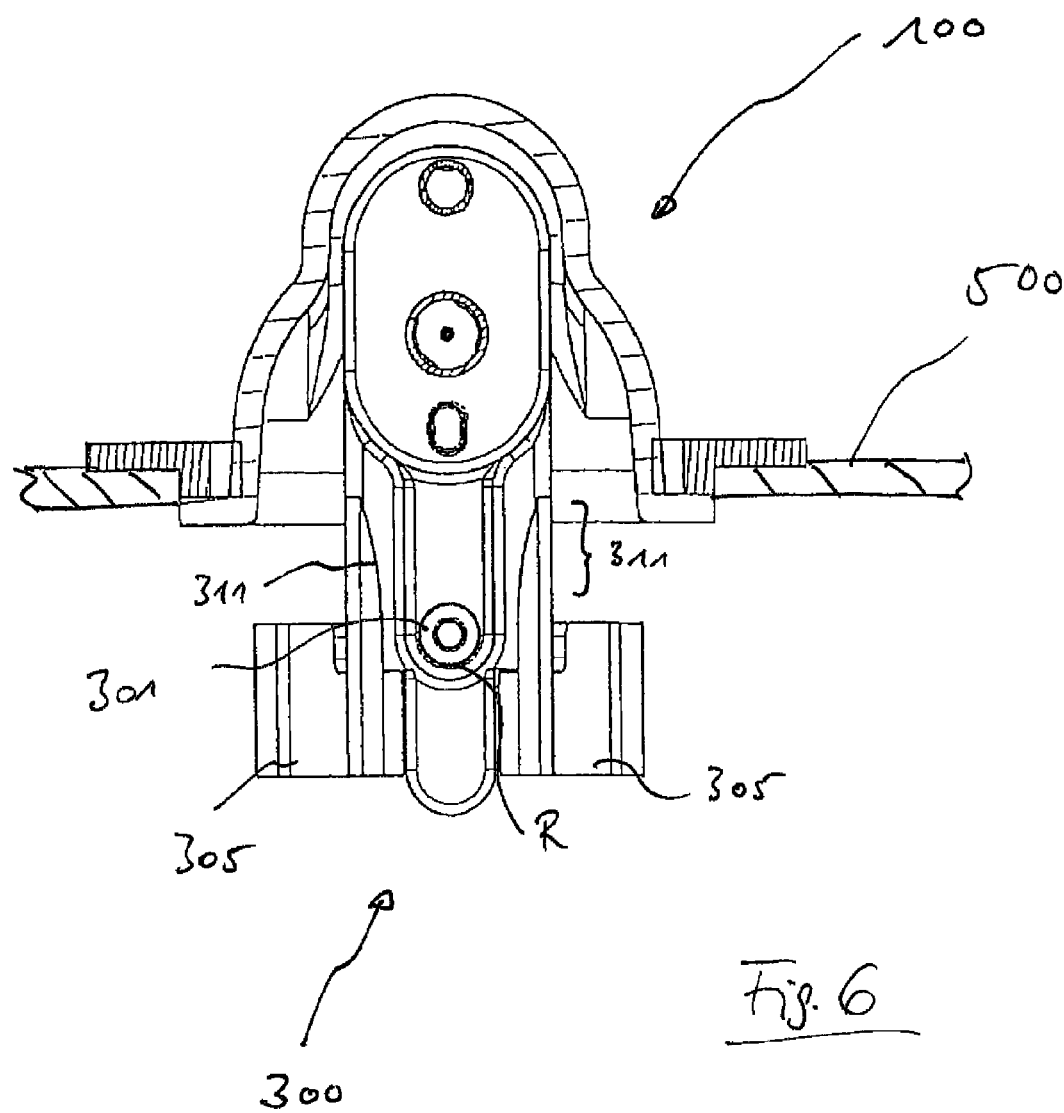
FIG. 6 shows the section of FIG. 4 in a top view.

FIG. 6 shows the section of FIG. 4 in a top view. The arc 311 of the front surface 309 is shown at both clamping devices 305.

In addition to the illustration of FIG. 4, a section of a housing of a blood treatment apparatus 500 according to the present invention is shown, in cross-section, in FIG. 6.

What is claimed is:

1. A clamp mounting for at least one of accommodating and restricting at least one section of a drug delivery device in at least one direction of motion, the drug delivery device having an accommodation chamber for a drug solution to be delivered, the clamp mounting comprising:
   at least one clamping device, the clamping device including at least one recess configured to at least one of accommodate and restrict at least one part of the section of the drug delivery device,
   wherein at least one of: (a) at least a section of the recess includes one of an arched and curved demarcation between the recess and sections of the clamping device that are not recessed, and (b) at least a section of the recess is one of arch-shaped and curve-shaped;
   wherein the recess is embodied as a groove;
   wherein the section of the recess that (a) includes one of an arched and curved demarcation and/or (b) is one of arch-shaped and curve-shaped, is bound on one side by a surface which is convex in a direction to a delivery opening for the drug in a plane parallel to a moving direction of the drug delivery device for the purpose of drug delivery, and is bound on an opposite side by a surface which is concave.

2. The clamp mounting according to claim 1, wherein the drug delivery device is a syringe, and wherein the section of the drug delivery device is a piston that is movable within the syringe for delivery of the drug solution.

3. The clamp mounting according to claim 1, further comprising:
 a support on which the drug delivery device rests with its section which is limited in its mobility by means of the clamping device in its state of use, when the section of the drug delivery device is at least one of accommodated and restricted by the clamping device,
 wherein the support has a rolling radius under which the support is rounded off at at least one transition of a supporting surface to one of a front surface and a lateral surface.

4. The clamp mounting according to claim 1, wherein the clamping device further includes at least one front surface having one of: (a) one of a curve and an arc, and (b) an area that is delimited in curve- or arch-shape.

5. The clamp mounting according to claim 1, wherein the clamping device one of: (a) further includes a spring, and (b) is connected to a spring.

6. The clamp mounting according to claim 1, wherein the at least one clamping device comprises two clamping devices configured to accommodate the section of the drug delivery device.

7. A dosing apparatus for dosing medical solutions or substances, comprising:
 at least one clamp mounting according to claim 1.

8. A blood treatment apparatus for extracorporeal treatment of blood of a patient, comprising:
 one of: (a) at least one clamp mounting according to claim 1, and (b) a dosing apparatus according to claim 7.

9. The blood treatment apparatus according to claim 8, wherein the blood treatment apparatus is an acute dialysis machine.

10. The blood treatment apparatus according to claim 8, wherein the blood treatment apparatus is one of a dialysis apparatus, a hemodialysis apparatus, a hemofiltration apparatus, and a hemodiafiltration apparatus.

11. The clamp mounting according to claim 1, wherein the recess is provided within the clamping device such that a first cross-section through the clamping device above the recess has the same shape as a second cross-section through the clamping device below the recess.

\* \* \* \* \*